US006333629B1

(12) United States Patent
Pykett et al.

(10) Patent No.: US 6,333,629 B1
(45) Date of Patent: Dec. 25, 2001

(54) METHOD FOR NON-INVASIVELY AND WITHOUT CONTACT, INSPECTING FOIL ENCLOSED PACKAGES, USING MAGNETIC RESONANCE TECHNIQUES

(75) Inventors: Ian L. Pykett, Saratoga Springs; Timothy W. Skloss, Green Island; Michael J. Hennessy, Ballston Lake, all of NY (US)

(73) Assignee: Intermagnetics General Corporation, Latham, NY (US)

( * ) Notice: Subject to any disclaimer, the term of this patent is extended or adjusted under 35 U.S.C. 154(b) by 0 days.

(21) Appl. No.: 09/359,176

(22) Filed: Jul. 22, 1999

(51) Int. Cl.⁷ ....................................... G01V 3/00
(52) U.S. Cl. .................. 324/307; 324/306; 324/300; 324/308
(58) Field of Search ................... 324/307, 306, 324/308, 318, 300

(56) References Cited

U.S. PATENT DOCUMENTS 5,270,650  12/1993  Schenz et al. ................ 324/308
5,371,464  * 12/1994  Rapoport ..................... 324/306

OTHER PUBLICATIONS

John Wiley & Sons, Inc., Magnetic Resonance Imaging In Food Science, Brian Hills, Institute of Food Research.

Scientific American, May 1982, vol. 246, No. 5, pp. 78–88, NMR Imaging In Medicine, Ian L. Pykett.

Critical Reviews in Food Science and Nutrition, vol. 36, Issue 4, 1996, Applications of Magnetic Resonance Imaging in Food Science, Shelly J. Schmidt, et al., pp. 357–385.

Low–Field MRI of Laser Polarized Noble Gas, G.H. Tseng et al, pp. 1–9.

* cited by examiner

Primary Examiner—Jay Patidar
Assistant Examiner—Brij B. Shrivastav
(74) Attorney, Agent, or Firm—Helfgott & Karas, PC.

(57) ABSTRACT

Increasing RF transmission power, retuning the RF transmitter and receiver coils, and increasing RF reception gain, enable MR inspection of product in a container that presents a substantial portion of an electrically conductive barrier in transverse orientation to the exciting RF magnetic field.

33 Claims, 1 Drawing Sheet

METHOD FOR NON-INVASIVELY AND WITHOUT CONTACT, INSPECTING FOIL ENCLOSED PACKAGES, USING MAGNETIC RESONANCE TECHNIQUES

BACKGROUND OF THE INVENTION

This invention relates generally to evaluation of the properties of a substance in a non-destructive, non-invasive, non-contacting manner, and more particularly to evaluation by using magnetic resonance techniques of the property of a substance or a material contained in discrete foil enclosed packages.

Magnetic resonance (MR) has been employed successfully in recent decades in both analytical and clinical sciences involving spectroscopy and imaging applications. MR spectroscopy and less often MR imaging are used as analytical tools in industrial laboratories as frequently as in academic laboratories. The migration of MR from a research laboratory to the manufacturing line and its transformation from a general purpose analytical or imaging technique into a specialized process control subsystem is a much more recent trend.

The generic advantages which have made MR so successful in its traditional role in medicine and research laboratories are equally valuable in manufacturing contexts. These advantages include non-invasive evaluations that are sensitive to many chemical and physical properties of matter, an ability to obtain results without contact and independently, even if the sample container is optically opaque. The requirements and environments of industrial plants as compared to those of hospitals or research laboratories, present new opportunities as well as challenges in using MR technology.

For example, in a manufacturing context there are fewer restrictions on the magnetic fields that can be applied to the sample. For example, the maximum magnetic field strength, the rate of change of magnetic field gradients, and RF heating and acoustic noise emission, can be much higher than allowed in a medical examination. Problems that have existed with noise and claustrophobic effects in MRI imaging of patients at hospitals may not be problems in industrial environments, thus allowing for greater flexibility in MR magnet design.

An unrelenting drive for improved productivity, higher product quality and greater product yield, as well as the wide spread adoption of international manufacturing standards and increasingly stringent governmental regulation, have driven industry to seek novel solutions to automated inspection and control of a diverse assortment of manufacturing processes. Magnetic resonance is becoming more recognized as a solution to many such problems. Many fundamental properties of liquids such as moisture content, bulk flow, diffusion, pH, viscosity, composition and temperature are amenable to analysis through MR techniques. In solids, internal flaws, porosity, uniformity and composition are amenable to analysis. MR has already been explored, for example, in analysis of foods and beverages, plastics and rubbers, petrochemicals, explosives, narcotics, fuel propellants, and even timber. MR is completely non-invasive, non-contacting and does not significantly change the nature of the sample being inspected.

For example, nuclear magnetic resonance (NMR) techniques have been applied as a sorting machine of watermelons. The hardware included an ordinary NMR imaging system (0.5 T, bore size of 68 cm in diameter). Sugar content of a watermelon was detected with high precision, better than 0.07 percent, by applying multiple regression analysis to observed relaxation times T1 and T2. Internal defects such as voids in watermelons have been detected by analyzing NMR signal intensities in an image. Voids can be detected and sorted with high accuracy and high speed i.e., at a rate of inspection of one second per piece.

The underlying concepts of magnetic resonance spectroscopy and magnetic resonance imaging are now generally well known and are not presented in detail herein. The basic physical concepts of MR and specialized techniques for three-dimensional imaging are described in *NMR Imaging In Medicine* by Ian L. Pykett (an inventor here), an article published in Scientific American, Volume 246, No. 5, May 1982, pages 78–88.

The published article *Application Of Magnetic Resonance In Food Science*, by Schmidt, Sun and Litchfield, Critical Reviews In Food Science And Nutrition, 36(4):357–385 (1996), also reviews the physical principles of MRI, describes various applications using MRI imaging, and illustrates the rapid progress in the art during the short interval between publication of the two above-referenced articles.

Current Methods: Spoilage Detection

The patent of Schenz et al., No. 5,270,650, issued Dec. 14, 1993, discloses techniques for non-destructive detection of spoilage in foodstuffs using nuclear magnetic resonance spectroscopy. The '650 patent is concerned with detection and measurement of bacterial activity within foodstuff containers. Bacterial action and foodstuff spoilage occurs, although not frequently, even in packaged foodstuff that has been sterilized after initial packaging or has been packaged under aseptic conditions. Prior to the spectroscopy methods described in the patent, quality control of packaged food stuff was maintained by several methods including a destructive method requiring the opening of a randomly selected container in order to test the nutritional product contained therein. The pH level is often considered an indicator of bacterial action, a drop in pH often indicating that the product is not sterile. This sampling is a destructive and time consuming test, that in high speed production, is only applicable to a limited number of containers out of a large batch of product.

Visual inspection for sterility may be possible when the product is in a container having transparent or translucent walls. This method is labor intensive and frequently inconclusive since the inspector may not always be able to detect visually the difference between contaminated and non-contaminated product.

Subculture methods from a small batch sample are unreliable and extremely late in providing results relative to a large production run, which is done at high rates of output.

There are many other tests for sterility described in the '650 patent; these tests can be replaced by non-invasive, non-destructive, rapid MR spectroscopy. In the patent, a nutritional product in a sealed container, transparent to RF, is inspected by MR techniques that determine the peak free induction decay value associated with the nutritional product. Changes in that property with passage of time, when that property is measured under similar conditions, indicate whether spoilage of the nutritional product has occurred. Alternatively, the determination of spoilage may be based on a comparison of immediate test results with previously established standards for that product.

The two articles and U.S. patent mentioned above are incorporated herein by reference.

MR inspection techniques cannot be applied in every situation. For example, MR was not considered to be applicable in the prior art to evaluation of samples which reside inside metallic or ferrous containers. Such containers generate interactions with the static magnetic field of the MR system and deleteriously affect the MR response signal. MR has also not been applied to some systems which contain nonferrous but electrically conducting materials, as such materials may severely attenuate and affect the homogeneity of the radio frequency magnetic field, inhibit field penetration into the sample, or generate undesirable eddy currents during a switched gradient operation, resulting in degradation of the resulting data.

Thus, it has not been considered possible to do MR inspection of a product that is entirely enclosed in a metal enclosure or even an enclosure including a complete barrier of metallic foil. It is well known in the prior art that an enclosure of metal, or of any electrically conductive material, provides a shield for the enclosure's contents from external electrostatic and electromagnetic fields. For example, pending application Ser. No. 08/974,291, filed Nov. 19, 1997, having several joint inventors who are inventors in the present application, describes an inspection system using MR pulse sequences for simultaneous inspection of multiple packages of food product with the packages positioned in a three dimensional physical configuration of the final shipping carton. Each package is individually, non-invasively evaluated without contact and already within the final shipping carton. Indication of any deviant package is provided.

However, the pending '291 application, which is hereby incorporated by reference, makes special note that only product packages that are at least partially transparent to RF magnetic fields operate successfully in the apparatus. Use of the apparatus to inspect product that was entirely or substantially enclosed in a metal or foil container was not considered possible at the time of the invention in the pending application. Thus, it was considered that many food products, which are preferably packaged in containers made of or including metallic foil as a barrier to atmospheric leakage, were never considered as subject to inspection with the MR apparatus of the pending application.

In summary, the "wishful thinking" of perhaps only 30 years ago for non-invasive, non-destructive testing of many materials and processes including agricultural products and packaged foodstuffs, has become realizable. Improved productivity, higher product quality, and greater product yield are now available by means of assessments at high speeds, substantially in real-time, and with a high level of reliability. Unfortunately, available MR inspection equipment and its inability to measure quality of product in metal cans and metallic foil enclosures, has limited use of such MR equipment and denied manufacturers, for example, in food industries, of the tremendous advantage of these non-invasive, high speed techniques.

What are needed are quality evaluation methods and associated apparatus for accelerated MR inspection for single or multiple characteristics of finished product, which methods and apparatus are non-destructive, non-contacting, and non-invasive, and operate on products in containers having an electrically conductive barrier separating the product from the ambient environment, a substantial portion of the barrier being positioned transversely to the RF magnetic field orientation during MR excitation.

SUMMARY OF THE INVENTION

Well-known to those skilled in the art of magnetic resonance, the following definitions are applicable in this application.

A "Static Magnetic Field" is a magnetic field with a magnitude that is nominally uniform over both Space and time;

A "Gradient Magnetic Field" is a magnetic field with a magnitude that varies nominally linearly (but at least monotonically) over Space and, depending on the particular experiment (which is defined by the Pulse Sequence), also with time;

A "Radio-frequency Magnetic Field" is a magnetic field with a magnitude that is nominally uniform over Space, and oscillates with a particular frequency, such frequency usually being within the band of frequencies commonly known as "radio-frequencies";

Where "Space" is a volume nominally similar to that of the object (or portion of object) under investigation, and "Pulse Sequence" defines the timing at which such magnetic fields are applied.

In accordance with the invention, finished product is evaluated for quality using MR techniques that enable inspection with regard to a selected parameter or parameters.

Advantageously, for adaptation of MR techniques to high speed production, an industrial plant manager is rarely interested in a picture of the product or product constituent, but rather wishes to receive a quantitative measurement of one or more very specific process related parameters. For example, in the Schenz, et al. patent, the presence of spoilage was detected in filled food containers, but there was no need for a picture which might show where the spoilage occurs in the container. Thus, the results from the MR data and an inspection station must be processed, but need not always be presented pictorially as in medical imaging. This may reduce the cost and complexity of the equipment.

In the present invention, MR equipment similar to that used in medical MR imaging of patients may operate with permanent magnets, resistive magnets or superconducting is magnets.

The product to be tested is carried in metal or metalfoil-lined containers, which contrary to prior knowledge, allow RF fields to penetrate so that these signals interact with the product in accordance with known MR techniques. Heretofore, MR techniques were applied under limited conditions. For example, a food supplement was evaluated, such as a ready-to-feed nutritional product that was enclosed in a plastic container with a plastic lid. The container could also be glass with a plastic lid, or the container could be partially of metal, for example a metallized plastic container and a plastic lid. On the other hand, the container could comprise an RF transparent plastic cup sealed with an aluminum foil metal cap as in the '291 application.

Successful operation of such hybrid constructions in the MR apparatus were believed to depend upon the amount and type of metal and its orientation with respect to the static magnetic and radio frequency magnetic fields. Simply stated, the product which was to be evaluated in the MR equipment was packaged as it would be sold to the consumer. However, the package was specially oriented during MR inspection and constructed to provide a required degree of RF transparency. A continuous barrier of metal did not separate the product from its external ambient environment. For example, the all-metal, integral cap discussed in the '291 patent was a circular aluminum disk with a narrow peripheral rim. Thereby, the cap itself was a shallow cup. In MR inspection, the narrow rim, a minor portion of the entire container surface, was oriented transversely to the RF magnetic field, but the circular disk portion, a substantial portion of the entire container surface, was set parallel to the RF field to minimize its disturbing effect on the magnetic resonance performance.

Never was it considered feasible that the same apparatus, with minor modification, could be used to inspect product entirely enclosed in a metal container or, for example, in a container that provides a substantially continuous metal foil barrier between the product and the ambient environment. Never before the present invention could any food products, such as UHT Milk (unrefrigerated fluid milk) in laminated containers of paper and metal foil, be inspected for bacterial contamination by MR techniques as they will be sold to the ultimate consumer, or as they are packaged for shipment to a vendor. UHT refers to the specific class of heat treatment regimen (Ultra High Temperature) that is used to sterilize the product.

For example, using the present invention, any spoilage within the individual UHT Milk food packages can be detected after the data gathered by the MR apparatus is processed and analyzed by computer.

With regard to foodstuffs in what is expected to be a sterile product, spoilage due to bacterial action is indicated by changes in the free induction decay (FID) during the MR evaluation. Whether spoilage is occurring in an individual food package is determined by comparing the MR characteristics of the product package against either a predetermined standard, a calculated "moving" value of production characteristics, or the results of a previous test on the same product package.

To inspect a product by MR techniques, which are described in greater detail in the 08/974,291 patent application, when the product is in a package that provides a substantially continuous metal or metal foil barrier, this heretofore impossible objective is accomplished by the following method. (1) Retuning the MR apparatus to the desired RF frequency. The retuning is necessary due to the geometry of the container and presence of the foil. (2) Increasing the power level of the RF magnetic field until sufficient field penetration and meaningful data are achieved. The increased power level of the RF magnetic field compensates for increased load on the RF transmitter coil due to the metal foil barrier. (3) Increasing gain on the RF receiver to provide sufficient output signal strength to produce meaningful data. (4) Repeating steps 2 and 3 as may be necessary until satisfactory data is obtained.

The degree of change to the apparatus depends upon the nature of the metallic barrier, its thickness relative to the RF frequency in use, the magnitude of static magnetic field in the MR apparatus, the configuration of the package and its foil and its orientation relative to the RF magnetic field. By adjusting these parameters, successful MR inspection of product substantially enclosed in a metallic or other conductive barrier, has been successfully effected.

The same MR and data assessment concepts may be applied with regard to other detectable parameters that may be deviant from accepted standards of a particular product. Missing, unfilled or partially filled packages can be identified. Sealed packages that have unwanted leakage can be detected, etc. Many additional applications will surely be found in the future.

Thus, a sealed product, even one packaged within a substantially continuous metal, metal foil, or other conductive barrier, can be evaluated, non-invasively, non-destructively, with no contact with the measuring device.

Accordingly, it is an object of the invention to provide improved apparatus and methods for evaluating a product, including those contained within a substantially continuous barrier of metal or metal foil, in a non-invasive, non-contacting, non-destructive manner.

Still other objects and advantages of the invention will in part be obvious and will in part be apparent in the specification.

The invention accordingly comprises the several steps and the relation of one or more such steps with respect to each of the others, all as exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which.

DESCRIPTION OF PREFERRED EMBODIMENTS

Figure 1A:
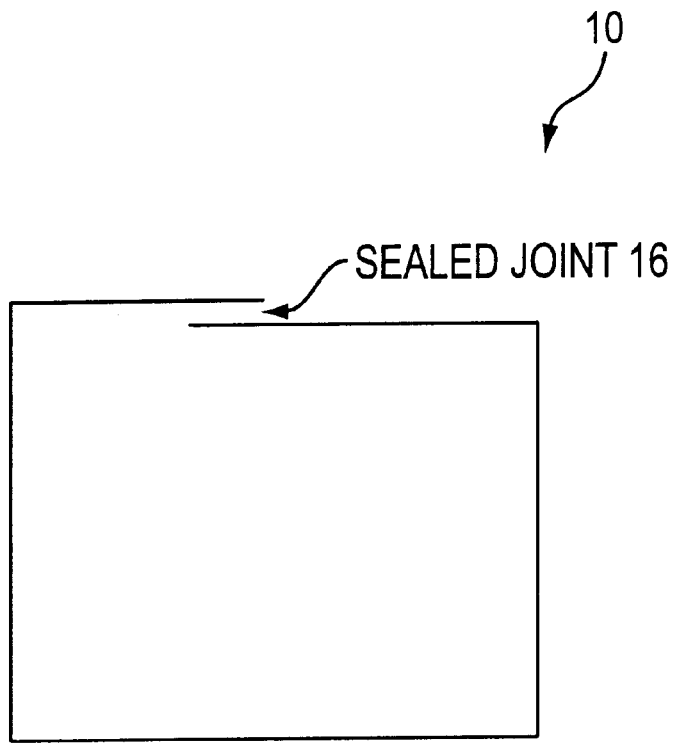
FIG. 1a is a cross section of a folded carton that may be MR inspected by the method in accordance with the invention.
Figure 1B:
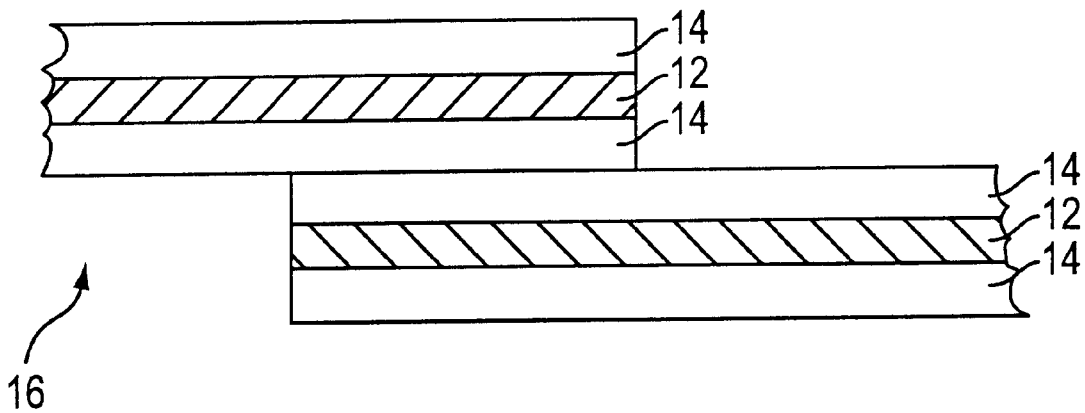
FIG. 1b illustrates (to an enlarged scale) an overlapping joint of the carton.

The application Ser. No. 08/974,291 represented a significant step forward in MR production monitoring of aseptically packaged products, which have nuclei that can be magnetically polarized by a static magnetic field. Such packaged products have a very low incidence of failures, thereby making traditional statistical sampling and testing methods inadequate for quality assurance. The goal of economic, 100% inspection for bacterial spoilage in a non-destructive manner was met in application '291. But, this success was achieved only with products packaged in a plastic or glass container with a thin foil aluminum lid or cap. In selecting the container, it was known in advance, if MR inspection was to succeed, that at least a portion of the container and its closure must sufficiently pass the in going RF inspection signals as well as the responsive RF signals from the stored product. Even use of a thin aluminum lid, particularly oriented during MR inspection, was questioned. The effect of the metal lid on ultimate results was unknown until actual testing was accomplished.

Thus, the '291 application provided a solution to a problem of 100% inspection of a product in a packaging that was constructed to particularly satisfy the then-known requirements for MR testing.

However, many other producers of packaged food products were not candidates to use the same methods and apparatus for 100% inspection of their production.

In fact, the majority of aseptically packaged foods, are currently enclosed in boxes that are substantially completely lined with aluminum foil. Successful inspection of such boxes by MR techniques, including those disclosed in '291, had demonstrated only the inadequacy of existing systems.

Boxes or cartons that are completely lined with aluminum foil are manufactured principally by major producers such as TetraPak, an industry leader, SIG Combibloc, and International Paper, among others. The cartons are manufactured from proprietary multi-layer laminates, where a paper layer provides stiffness and strength. Polymer layers seal the carton so that it is liquid tight, and aluminum foil keeps out light and oxygen, which can degrade the stored product.

For example, TetraPak offers fruit juice and milk, which require no refrigeration, in laminated paper/aluminum foil boxes. With these milk products, the attractiveness of extended shelf life without deterioration of product is provided by the laminated, metal-lined package. However, 100% inspection of product as it is produced was not economically available, not even by MR techniques. While successful in inspecting cases filled with product in glass or plastic cups having only an aluminum cap, the method and apparatuses of the '291 application produced no MR response on commercially available food products, such as the above mentioned fruit juice and milk, in paper/aluminum foil cartons. In these situations, the foil barrier is substantially complete and presents substantial foil portions that are transverse to the RF field, regardless of the orientation of the carton/package in the MR apparatus. The product is substantially enclosed by the barrier.

Also, it was known that electromagnetic fields can penetrate into conducting materials by a penetration if distance called the "skin-depth". It is well known that the thinner the metallic barrier, the more likely it is to be penetrated by an electromagnetic field. Further, lower nuclear magnetic resonance frequency signals can penetrate much deeper into the conducting materials than higher frequencies. As is well known, the static magnetic field strength in a MR apparatus determines the excitation and signal response frequencies. In most existing MR apparatuses, static field strength is substantially fixed; thereby, the operating RF frequencies are similarly substantially fixed, being proportional to the static magnetic field strength.

Experimentation was begun to disprove or confirm that conventional MR signals would not enter a metal lined package and provide return signals indicative of characteristics of the contained product. In these tests, apparatus was used having a substantially constant static magnetic field and therefore a substantially constant Larmor frequency. Thus, the variables for initial experimentation were the thickness of the metal barrier, power level for the RF transmitter of the MR apparatus, and RF receiver sensitivity or gain.

For test purposes, a juice box, manufactured by Tetra Pak was selected. The box was a foil-lined container used commercially for holding room temperature foods. A cross-section of the wall consisted of a metallic aluminum foil, laminated on both sides with paper. The aluminum foil was approximately 6 microns to 7 microns thick. Calculations indicated that signal and power loss through the foil would be 4 dB at 6.3 MHz (0.15 T) based on a localized skin-depth model. Nevertheless, there were calculated indications that, despite attenuation, a signal would be detectable if sufficient power were applied in the RF excitation signal.

First experiments with the foil container indicated that the RF power requirements were much higher than the requirements for normal imaging as described in the '291 application, where the product was in a package that was mostly transparent to the RF signal. Lacking RF power, an NMR signal (FID) was first recorded from the foil container contents but a conventional spin echo image was not obtainable. Acceptable results were achieved, including gradient spin echo, at low flip angles (nutation angles) when using a larger coil where RF power was otherwise limited. A 180° pulse was subsequently achieved with a smaller RF coil and a spin echo image was recorded.

Additional measurements were made in a test apparatus on the transmission of power through an empty foil fruit juice package. For example, a RF transmission measurement was made at 6 MHz through the empty package using two coils, a transmitter coil mounted outside the package and a receiver coil mounted inside the package. Both coils were connected to a network analyzer. Measurements indicated that the RF power was attenuated 20 dB going through the foil. In effect, the RF field was reduced by a factor of 10 in passing through the container. Thus RF power required in this test to generate an excitation pulse in the container was 100 times higher than for a non-metallic container.

Because there is reciprocity between transmission and reception, the MR signal was also attenuated by approximately 20 dB.

Nevertheless, the long held belief that a metallic enclosure would effectively shield the contents of the enclosure from external RF radiation, was disproved, at least in the frequency range of the testing. Contrary to preconceptions, the benefits of a metal enclosed food package and 100% non-destructive inspection, at high speed, were in fact available to industry.

Based on this work, a methodology was developed to modify an MR apparatus that was originally used for inspecting packages substantially of a non-metallic, non-conductive barrier construction, to an apparatus in accordance with the invention for inspecting a container including a substantially complete conductive barrier. The method may be used where static magnetic field and the associated Larmor frequency are substantially constant in the MR apparatus(or the frequency has been preset in an apparatus with an adjustable static field).

1. Tuning the RF transmitting coil and RF receiving coil of the MR apparatus with the package in place having the substantially enclosing conductive barrier containing the product. That is, the package is located where the package would normally be inspected during a test. A metallic foil package severely perturbs a free air RF coil to the extent that it is virtually necessary that the sample should be in place when tuning the coil. This tuning to the Larmor frequency may even require a change in electronic components, for example, capacitors. It should be understood that whereas separate transmitting and receiving coils are indicated here, it is well-known in the art that a single tuned coil can be used for both transmitting and receiving purposes by passive or active multiplexing techniques.

2. Increasing the level of RF power transmitted by the RF coil until an FID response is visible from the container contents after the data is processed. When sufficient power is available, the RF power is increased until the full 90° or 180° pulse is observed. Alternatively, if available power is insufficient for a 90° pulse, a low flip angle sequence and shaped RF pulses can be used, as is well known to those skilled in the MR arts. The increase in power level (dB) is directly related to the attenuation (dB) of the foil alone. Thus, preliminary tests on an empty container may provide valid indications of incremental power and total power requirements.

3. Adjusting the RF receiver gain to a usable level during step 2. This receiving step requires an augmented gain, substantially increased by the same decibel level or higher as the increment in transmission in step 2, to achieve an output signal equivalent to that signal which would be received from the same sample contained in an equivalent glass or plastic (RF transparent) container.

It should be noted that both the transmission power and receiving gain are increased in order to achieve an equivalent output signal when using the method of the present invention on containers that at least substantially enclose the product with a conductive barrier and/or have substantial portions of the barrier transverse to the RF magnetic field. If the glass or plastic container of the '291 application with its aluminum cap were subjected to increased RF transmission, it would be expected that receiver gain would have to be decreased (attenuation increased) to achieve an equivalent output signal (assuming the nutation angle remained correct).

Basically, the transmitter gain has to be adjusted only to the point that the required RF nutation (e.g.: 90 degrees; 180 degrees; etc.) is achieved. If there is less "transverse" foil, less RF power will be needed to achieve that required nutation. If the glass or plastic container of the '291 application were subjected to increased RF transmission, the nutation angles in reality would likely be incorrect. The RF excitation energy would have to be reduced. It is true, however, that, when the transmit RF energy is set to provide the correct nutation angles in each case (foil and no-foil), the receiver attenuation would be expected to be higher (lower gain) for the "RF transparent" carton than for the "RF 'opaque'" carton.

At the present stage of development, most current MR techniques appear to be applicable for use with "shielded" enclosures when the MR apparatus is adjusted in accordance with the present invention, including CPMG, spin echo imaging, etc. Images may have some RF artifacts, particularly near the corners of rectangular product containers. These artifacts appear to be dependent on the geometry and orientation of the container in the MR apparatus as would be anticipated from Eddy current analysis.

As stated, when available RF power is limited, low flip angle gradient echo imaging can be viable. In such situations, the available RF power tips only a fraction of the magnetization in the measurement plane. The loss of signal due to reduced flip angle is recovered by shortening the TR as in conventional magnetic resonance. An optimum flip angle can be found for a given set of T1 and T2 values.

As known to those skilled in the art, use of reduced flip angle may be effective where available RF power is low. However, such conditions usually deteriorate the signal to noise ratio as compared to higher RF power operation. Thus, in some cases, a more efficient RF coil may be necessary for delivering higher power level and for increasing the signal to noise ratio of the measurement. Further, cryoprobes or high temperature superconducting coils can be used for some measurements to increase the sensitivity of the receiver if signal to noise ratio presents difficulties.

The MR techniques of the present invention are applicable to spoilage and/or leak detection in dealing with a production line of food products and in other evaluations as discussed in the '291 application.

The present invention changes the definition of "RF opaque" in relation to MR inspection. Such RF opaque materials had included all metals, steels, aluminum, brass, copper, etc., and any other class of material which is electrically conductive and has an RF penetration depth (skin depth) less than the package wall thickness. Electrically conductive nonmetallic materials included graphite, commonly in the form of graphite fiber/resin composites. Also included in the list of unacceptable materials were conductive ceramics and polymers, metallized plastics, and conductive fluids such as sea water. While sea water is not likely to be part of many food products, it is noteworthy that human bodies have similar electrical properties to sea water and the conductive nature of the body limits the range of medically useful MR frequencies.

Now it is known by the methods of the present invention, that a package can be successfully inspected by MR techniques even when that package includes a substantially continuous barrier of aluminum foil substantially enclosing the product. This is an important property for aluminum foil in that, as stated above, many food manufacturers use such foil and foil laminates in packaging their products. The aluminum foil provides a barrier against in-leakage of external environmental air. Thus, extended storage of a sterile food product is possible. A non-defective package, which is found sterile by MR techniques when the product leaves the production line, will remain in the desired sterile condition.

Therefore, extensive MR related development work to date by the present inventors has been applied to aluminum foil containers or laminates including aluminum foil because of the general commercial usage of such packaging. However, other materials previously considered to be unsuitable for MR inspection, as indicated above, may also prove responsive to the methods of the present invention, wherein RF transmission is augmented and RF reception is made more responsive to enhance low level signals.

The opacity of a material to RF depends upon the electrical conductivity of the material, its thickness, and the frequency of the radio frequency magnetic field. Thus, other materials previously considered as completely opaque may still be subject to measurements by modified MR methods of the present invention.

An RF frequency magnetic field is applied to the sample in the apparatus described above to excite the MR signal from the sample. It is only the magnetic component of the RF electromagnetic energy that excites spins as is well known in the art. The RF receiver detects a signal which is an oscillating RF magnetic field. Whereas an RF coil was used to detect that magnetic field in the description above, the RF magnetic signals may be detected directly, for example, by SQUIDs rather than by standard RF coils.

The '291 application provides substantially simultaneous inspection for arrays including a plurality of prepositioned product packages. On the other hand, to inspect one product package at a time, spatial encoding is not required, and the pulse sequence of RF fields may be simplified.

The method of the present invention successfully inspects laminated cartons as described above. Such cartons, for example, with a thin layer of aluminum foil sandwiched between RF translucent layers, for example, polymer laminates, paper, are characterized in that the aluminum foil substantially encloses the product in a continuous electrically conductive barrier. This container is distinguished from the container in the '291 application that was substantially of glass or plastic but had a thin aluminum cap. The '291 aluminum cap was carefully oriented during MR testing so that only a very narrow hoop of aluminum was oriented transversely to the exciting magnetic MR field.

The present method requires no such careful orientation for the aluminum foil-lined cartons, although orientation cannot be ignored in an interpretation of test results. Stated otherwise, the present method is effective for MR inspection even when substantial portions (at least 10% by area) of the conductive barrier are oriented transversely to the RF magnetic field. Inspecting a rectangular carton, such as used for long-life unrefrigerated milk and juice products, that includes a continuous or substantially complete foil layer, would clearly fall within the scope of the present invention. Substantial portions of the aluminum foil would be oriented transversely to the magnetic RF field regardless of the orientation of the carton itself in the MR apparatus. On the other hand, the container of the '291 application is not considered to fall within the scope of the present invention because only the negligible (in comparison to the entire surface area of the container) rim hoop of aluminum is transversely oriented to the RF magnetic field after careful positioning of the test package in the MR apparatus.

The immediately above paragraphs discuss a rectangular carton having a perfect continuous aluminum foil (or conductive material) barrier that entirely encloses the product. The present invention is intended to include inspection by MR techniques of such a "perfectly" enclosed product. However, from a practical point of view, whereas the number of such cartons in daily manufacture is astronomical, the perfect barrier is not always achieved. The product may not be entirely and continuously enclosed within the aluminum foil but, in fact, may be and generally is only "substantially enclosed" in the foil barrier. The perfect foil enclosure may not be achieved, for example, because the carton may require a small opening, which is covered by a (flip) cap that is made, for example, of RF-transparent plastic. This gap may break the electrical conductivity of the foil and allow RF penetration. For purposes of this application, it is considered that such an opening in the foil (or any other opening), small (less than 10%) in relation to the overall area of the carton (and not detrimental to the contained product), leaves the product in a "substantially enclosed" state with regard to the foil barrier.

As another example, in manufacturing the carton, sheets of the laminated carton material may be folded and joined together as illustrated in FIGS. 1a,b. The basic sheet material of the carton 10 includes the thin aluminum foil 12 and external paper layers 14. Other sealing layers (not shown) of plastic may be utilized as a liquid barrier at the joint and/or on other carton surfaces. Thus, at the overlapping joint 16, manufacturing economy dictates that the basic laminated sheet is sheared, folded and bonded without special foil treatment. The aluminum foil itself is not in continuous contact with the aluminum foil of the overlapped adjoining layer. A double layer 14, 14 of the paper material in this illustration separates the foil layers 12. Thus, a relatively narrow unshielded window 16 remains between the folds allowing RF magnetic fields to penetrate. For purposes of the present application, a foil lined carton, constructed with at least some of its joints having such minimal gaps in the foil's continuity, is considered as providing a "substantially enclosed" product.

Prior to the present invention, such containers or cartons, even with their RF-imperfect overlapping joints and small RF translucent plastic flip caps over a small opening, could not be inspected by MR techniques including those set forth in the '291 application. A product entirely enclosed by a conductive barrier also could not be successfully inspected.

The present invention makes possible, and practically feasible, MR inspection of such packages. This inspection is accomplished even when the package includes a perfect, entirely continuous conductive barrier and/or when a substantial portion of the electrically conductive barrier that surrounds the product is oriented transversely to the orientation of the RF magnetic field during MR inspection. Signals enter the product through the carton walls for inspection purposes and signals generated by the product within the carton are successfully received and analyzed through the carton walls.

It will thus be seen that the objects set forth above, among those made apparent from the preceding description, are efficiently attained and certain changes may be made in carrying out the above method without departing from the spirit and scope of the invention. It is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention, which as a matter of language might be said to fall therebetween.

What is claimed is:

1. A method for inspecting a product having nuclei that can be magnetically polarized by a static magnetic field, comprising the steps of:

(a) providing at least one product having said nuclei, said product being enclosed in a container including an electrically conductive barrier at least partially surrounding said product;

(b) providing a MR apparatus for inspecting said at least one product in said container, said apparatus having means for generating a static magnetic field, RF transmitting means and RF receiving means;

(c) positioning said container in said MR apparatus for inspection;

(d) exciting said product in said container with an RF magnetic field generated by said RF transmitting means of said MR apparatus, at least a substantial portion of said electrically conductive barrier being oriented transversely to an orientation of said RF magnetic field during excitation;

(e) receiving by said RF receiving means an RF signal from said at least one product in said container, said RF signal being a result of said excitation of said at least one product by said MR apparatus;

(f) processing and analyzing said received RF signal to determine data of said at least one product.

2. A method for inspecting a product as in claim 1, further comprising a step of selecting a level of RF transmission by said transmitting means, and a gain of said RF receiving means to effect said MR inspection of said product through said container including said electrically conductive barrier portion.

3. A method as in claim 1, wherein said barrier includes at least one of a metal foil, a metalized coating on an RF-translucent substrate, a conducting polymer and a conducting ceramic.

4. A method as in claim 3, wherein said barrier is a non-magnetic material.

5. A method as in claim 3, wherein said foil and coating include aluminum.

6. A method as in claim 1, wherein said MR excitation includes at least one of 90° and 180° RF excitation pulses for spin echo data acquisition.

7. A method as in claim 1, wherein said MR excitation includes low flip angle and shaped RF pulses for FID data acquisition.

8. A method as in claim 2, wherein said RF transmission output level and said RF receiving means gain are selected respectively higher than said output level and gain required for said MR excitation and receiving when said transversely oriented portion of said barrier is not present.

9. A method as in claim 1, wherein said output level and gain are higher when effectively inspecting a container with said transversely oriented portion of said barrier enclosing said product as compared to inspecting a container without a transversely oriented portion of a barrier.

10. A method as in claim 2, wherein RF power requirements for effective excitation are dependent on a thickness of said electrically conductive barrier and a RF frequency of said RF transmitting means.

11. A method as in claim 8, wherein positioning said container in step (c) detunes said RF transmitting means, and further comprising the step of retuning said transmitting means prior to step (d) when switching from inspecting a product without said transversely oriented barrier portion to inspecting a product with said transversely oriented barrier, said transmitting means being retuned to be close to a Larmor frequency of said MR apparatus.

12. A method as in claim 1, wherein said data is provided for detecting a deviant product.

13. A method as in claim 12, wherein said at least one product is a product subject to at least one of spoilage, chemical action, and leakage while in the container, a response of said at least one product to said excitation in said MR apparatus changing relative to a standard of value due to said at least one of spoilage, chemical action and leakage, said changing causing a data change as an indication by said MR apparatus of deviant product.

14. A method as in claim 8, wherein positioning said container in step (c) detunes said RF receiving means, and further comprising the step of retuning said receiving means prior to step (d) when switching from inspecting a product without said transversely oriented barrier portion to inspecting a product with said transversely oriented barrier, said receiving means being retuned to be close to a Larmor frequency of said MR apparatus.

15. A method as in claim 1, wherein said container barrier leaves unprotected less than 10% of the surface area of said container.

16. A method for inspecting a product having nuclei that can be magnetically polarized by a static magnetic field, comprising the steps of:
   (a) providing at least one product having said nuclei, said product being enclosed in a container including an electrically conductive barrier which substantially encloses said product;
   (b) providing a MR apparatus for inspecting said at least one product in said container, said apparatus having means for generating a static magnetic field, RF transmitting means and RF receiving means;
   (c) positioning said container for inspection in said MR apparatus;
   (d) exciting said product in said container with an RF magnetic field generated by said RF transmitting means of said MR apparatus, at least a substantial portion of said electrically conductive barrier being oriented transversely to an orientation of said RF magnetic field during excitation;
   (e) receiving by said RF receiving means an RF signal from said at least one product in said container, said RF signal being a result of said excitation of said at least one product by said MR apparatus;
   (f) processing and analyzing said received RF signal to determine data of said at least one product.

17. A method for inspecting a product as in claim 16, further comprising a step of selecting a level of RF transmission by said transmitting means, and a gain of said RF receiving means to effect said MR inspection of said product through said container including said electrically conductive barrier.

18. A method as in claim 16, wherein said barrier includes one of a metal foil, a metalized coating on an RF-translucent substrate, a conducting polymer, and a conducting ceramic.

19. A method as in claim 18, wherein said foil and coating include aluminum.

20. A method as in claim 17, wherein said RF transmission output level and said RF receiving means gain are selected respectively higher than said output level and gain required for said MR excitation and receiving when said substantially enclosing barrier is not present.

21. A method as in claim 16, wherein said output level and gain are higher when effectively inspecting a container with said barrier which substantially encloses said product as compared to effectively inspecting a container without a barrier which substantially encloses said product.

22. A method as in claim 20, wherein positioning said container in step (c) detunes said RF transmitting means, and further comprising the step of retuning said transmitting means prior to step (d) when switching from inspecting a product without said substantially enclosing barrier to inspecting a product with said substantially enclosing barrier, said transmitting means being retuned to be close to a Larmor frequency of said MR apparatus.

23. A method as in claim 20, wherein positioning said container in step (c) detunes said RF receiving means, and further comprising the step of retuning said receiving means prior to step (d) when switching from inspecting a product without said substantially enclosing barrier to inspecting a product with said substantially enclosing barrier, said receiving means being retuned to be close to a Larmor frequency of said MR apparatus.

24. A method as in claim 14 wherein said container barrier leaves unprotected less than 10% of the surface area of said container.

25. A method for inspecting a product having nuclei that can be magnetically polarized by a static magnetic field, comprising the steps of:
   (a) providing at least one product having said nuclei, said product being enclosed in a container including an electrically conductive barrier which entirely encloses said product;
   (b) providing a MR apparatus for inspecting said at least one product in said container, said apparatus having means for generating a static magnetic field, RF transmitting means and RF receiving means;
   (c) positioning said container for inspection in said MR apparatus;
   (d) exciting said product in said container with an RF magnetic field generated by said RF transmitting means of said MR apparatus, at least a substantial portion of said electrically conductive barrier being oriented transversely to an orientation of said RF magnetic field during excitation;
   (e) receiving by said RF receiving means an RF signal from said at least one product in said container, said RF signal being a result of said excitation of said at least one product by said MR apparatus;
   (f) processing and analyzing said received RF signal to determine data of said at least one product.

26. A method for inspecting a product as in claim 25, further comprising a step of selecting a level of RF transmission by said transmitting means, and a gain of said RF receiving means to effect said MR inspection of said product through said container including said electrically conductive barrier.

27. A method as in claim 25, wherein said barrier includes one of a metal foil, a metalized coating on an RF translucent substrate, a conducting polymer, and a conducting ceramic.

28. A method as in claim 27, wherein said foil and coating include aluminum.

29. A method as in claim 26, wherein said RF transmission output level and said RF receiving means gain are selected respectively higher than said output level and gain required for said MR excitation and receiving when said entirely enclosing barrier is not present.

30. A method as in claim 25, wherein said output level and gain are higher when effectively inspecting a container with said barrier which entirely encloses said product as compared to effectively inspecting a container without a barrier which entirely encloses said product.

31. A method as in claim 29, wherein positioning said container in step (c) detunes said RF transmitting means, and further comprising the step of retuning said transmitting means prior to step (d) when switching from inspecting a product without said entirely enclosing barrier to inspecting a product with said entirely enclosing barrier, said transmitting means being retuned to be close to a Larmor frequency of said MR apparatus.

32. A method as in claim 29, wherein positioning said container in step (c) detunes said RF receiving means, and further comprising the step of retuning said receiving means prior to step (d) when switching from inspecting a product without said entirely enclosing barrier to inspecting a product with said entirely enclosing barrier, said receiving means being retuned to be close to a Larmor frequency of said MR apparatus.

33. A method as in claim 25 wherein said container barrier leaves unprotected less than 10% of the surface area of said container.

\* \* \* \* \*